United States Patent
Mesangeau et al.

(10) Patent No.: US 8,592,370 B2
(45) Date of Patent: Nov. 26, 2013

(54) COMBINATION OF INSULIN WITH TRIAZINE DERIVATIVES

(75) Inventors: Didier Mesangeau, Combs la Ville (FR); Daniel Cravo, Sartrouville (FR); Annick Audet, Leudeville (FR)

(73) Assignee: Poxel S.A.S., Lyons (FR)

( * ) Notice: Subject to any disclaimer, the term of this patent is extended or adjusted under 35 U.S.C. 154(b) by 30 days.

(21) Appl. No.: 13/139,027

(22) PCT Filed: Nov. 13, 2009

(86) PCT No.: PCT/EP2009/008099
§ 371 (c)(1), (2), (4) Date: Aug. 29, 2011

(87) PCT Pub. No.: WO2010/066326
PCT Pub. Date: Jun. 17, 2010

(65) Prior Publication Data
US 2011/0306543 A1    Dec. 15, 2011

(30) Foreign Application Priority Data
Dec. 12, 2008 (EP) .................................... 08021617

(51) Int. Cl.
- A61K 38/28 (2006.01)
- A61K 38/00 (2006.01)
- A61K 31/53 (2006.01)

(52) U.S. Cl.
USPC ............... 514/6.5; 514/5.9; 514/6.7; 514/6.8; 514/6.9; 514/241; 514/245

(58) Field of Classification Search
USPC .............. 514/6.5, 5.9, 6.7, 6.8, 6.9, 241, 245, 514/866
See application file for complete search history.

(56) References Cited

U.S. PATENT DOCUMENTS

| | | | |
|---|---|---|---|
| 3,172,814 A * | 3/1965 | Ferguson, Jr. ................... | 514/6.5 |
| 5,858,024 A * | 1/1999 | De Lacharriere et al. ......... | 8/408 |
| 7,034,021 B2 * | 4/2006 | Moinet et al. ................. | 514/245 |
| 2002/0143015 A1 | 10/2002 | Fryburg et al. | |
| 2005/0165022 A1 | 7/2005 | Moinet et al. | |
| 2008/0108591 A1 | 5/2008 | Moinet et al. | |

FOREIGN PATENT DOCUMENTS

| WO | WO 01/55122 A1 | 8/2001 |
|---|---|---|
| WO | WO 2004/065387 A1 | 8/2004 |
| WO | WO 2007/079914 A2 | 7/2007 |
| WO | WO 2007/079917 A2 | 7/2007 |

OTHER PUBLICATIONS

International Search Report of PCT/EP2009/008099 (Feb. 5, 2010).
M.G. Wulffele et al., "Combination of Insulin and Metformin in the Treatment of Type 2 Diabetes", Diabetes Care, vol. 25, No. 12 (Dec. 2002) pp. 2133-2140.
H. Yki-Jarvinen, "Combination Therapies With Insulin in Type 2 Diabetes", Diabetes Care, vol. 24, No. 4 (Apr. 2001) pp. 758-767.
S.M. Strowig et al., "Comparison of Insulin Monotherapy and Combination Therapy With Insulin and Metformin or Insulin and Troglitazone in Type 2 Diabetes", Diabetes Care, vol. 25, No. 10 (Oct. 2002) pp. 1691-1698.
U. Beise, "Typ-2-Diabetes Insulin Plus Orale Antidiabetika", Ars Medici Dossier, vol. VII (Dec. 31, 2007) pp. 16-18.

* cited by examiner

*Primary Examiner* — Kevin E Weddington
(74) *Attorney, Agent, or Firm* — Millen, White, Zelano & Branigan, P.C.

(57) ABSTRACT

The invention relates to a composition for use as a medicament comprising insulin in combination with at least one compound of formula (I)

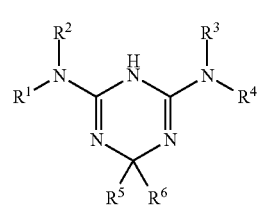

wherein the radicals $R^1$ to $R^6$ have the meaning according to claim 1, and/or physiologically acceptable salts thereof. Another object of the invention concerns a pharmaceutical composition comprising as active ingredients effective amounts of insulin and at least one compound of formula (I), together with pharmaceutically tolerable adjuvants, for the prophylactic or therapeutic treatment and/or monitoring of physiological and/or pathological conditions that are associated with insulin resistance. The invention also relates to a pharmaceutical package comprising insulin in a first dosage unit and at least one compound of formula (I) in a second dosage unit.

6 Claims, 2 Drawing Sheets

COMBINATION OF INSULIN WITH TRIAZINE DERIVATIVES

The invention relates to a composition for use as a medicament comprising insulin in combination with at least one compound of formula (I)

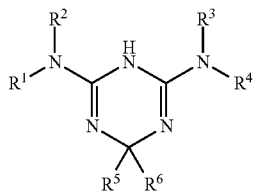

wherein the radicals $R^1$ to $R^6$ have the meaning according to claim 1, and/or physiologically acceptable salts thereof. Another object of the invention concerns a pharmaceutical composition comprising as active ingredients effective amounts of insulin and at least one compound of formula (I), together with pharmaceutically tolerable adjuvants, for the prophylactic or therapeutic treatment and/or monitoring of physiological and/or pathological conditions that are associated with insulin resistance (IR). The invention also relates to a pharmaceutical package comprising insulin in a first dosage unit and at least one compound of formula (I) in a second dosage unit.

Metabolic diseases such as obesity, IR and dyslipidemia are emerging as dominant causes of morbidity and mortality worldwide. Especially over the last decades, IR has become a highly prevalent condition in the general public, with enormous consequences for the public health system. IR is defined as the reduced, non-adequate response of the body to the normal actions of insulin. IR is an important risk factor for the development of cardiovascular disease and Type II diabetes mellitus (T2DM). Diabetes is a chronic disease with many pathological manifestations. It is accompanied by disorders of lipid and sugar metabolism as well as circulatory disorders. In addition, IR is associated with a variety of cardiovascular risk-factors (e.g. obesity, dyslipidemia, hypertension and blood clotting disturbances) that when exhibited collectively is referred to as the metabolic syndrome or syndrome X. Thus, insulin resistance syndrome (syndrome X) is characterized especially by a reduction in the action of insulin (Presse Médicale (1997), 26(14): 671-677) and is involved in many pathological conditions as mentioned above, particularly diabetes, more particularly non-insulin dependent diabetes, but additionally certain macro-vascular complications, e.g. atherosclerosis, or micro-vascular complications, e.g. retinopathies, nephropathies and neuropathies. Considerable evidence now exists that IR may be the unifying causal factor underlying the metabolic syndrome (Turner & Hellerstein (2005) Curr Opin Drug Discovery & Develop 8(1): 115-126).

Current therapeutic interventions aiming to directly improve the insulin responsiveness of the tissues apply thiazolidinediones (TZDs). However, while the TZDs have been shown to improve whole-body insulin sensitivity, they recently have become known to increase the risk of heart failure. Therefore, alternatives for the treatment of IR are necessary in the fight against the growing epidemic of deranged metabolic diseases, with one of its features being IR.

It is also known to apply insulin as an agent for treating type I diabetes (or insulin-dependent diabetes). Insulin is also used as a hypoglycemiant agent in the treatment of non-insulin-dependent diabetes. The prior art of EP 0 193 256 and EP 0 207 581, respectively, teaches thiazolidine-2,4-dione derivatives as anti-hyperglycemiants and hypolipemiants and thus, the compounds have been disclosed as anti-diabetic agents. These compounds are additionally activators of the peroxisome proliferator-activated receptor γ (PPARγ). The combination of certain PPARγ thiazolidine-2,4-dione derivatives, such as rosiglitazone, with insulin, has already been described for treating diabetes by SmithKline Beecham in the patent application WO 1998/57636. However, insulin doses remain high and come along with weight gain.

Therefore, the technical problem forming the basis of the present invention is to provide a pharmaceutical composition allowing an effective application in the prevention or therapy of diseases that are associated with insulin resistance, especially such compositions that improve the therapeutic efficacy and minimize adverse effects.

The present invention solves this problem by providing a composition for use as a medicament comprising insulin in combination with at least one compound of formula (I) and/or physiologically acceptable salts thereof, wherein the compound of formula (I) is defined as follows:

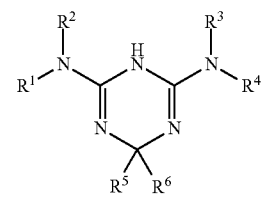

in which
$R^1$, $R^2$ each, independently of one another, denote H or A,
$R^3$, $R^4$ each, independently of one another, denote H, A, alkenyl having 2-6 C atoms, alkynyl having 2-6 C atoms, Ar or Het,
$R^5$ and $R^6$ together also denote alkylene having 2, 3, 4 or 5 C atoms,
$R^5$, $R^6$ each, independently of one another, denote H, A, $(CH_2)_nAr$, $(CH_2)_mOAr$, $(CH_2)_mOA$ or $(CH_2)_mOH$,
$R^5$ and $R^6$ together also denote alkylene having 2, 3, 4 or 5 C atoms, in which one $CH_2$ group may be replaced by O, NH or NA and/or in which 1 H atom may be replaced by OH,
Ar denotes phenyl, naphthyl or biphenyl, each of which is unsubstituted or mono-, di- or trisubstituted by Hal, A, OA, OH, COOH, COOA, CN, $NH_2$, NHA, $NA_2$, $SO_2A$ and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, OH, OA, $NH_2$, $(CH_2)_nAr$, NHA, $NA_2$, COOH, COOA and/or =O (carbonyl oxygen),
A denotes unbranched or branched alkyl having 1-10 C atoms, in which 1-7 H atoms may be replaced by F, or cyclic alkyl having 3-7 C atoms,
Hal denotes F, Cl, Br or I,
m denotes 1, 2, 3, 4, 5 or 6, and
n denotes 0, 1 or 2.

It has been surprisingly demonstrated by the inventors that the triazine compounds of formula (I) and derivatives thereof can be applied as active ingredients in a pharmaceutical combined composition with insulin in order to tackle medical indications arising from IR, such as diabetes, and diseases being linked therewith. Before filing this application, it has only been known that compounds of formula (I) can be prepared by processes according to WO 2001/55122. The compounds of formula (I) might be useful in the treatment of diseases associated with the IR syndrome. Representatives are currently under clinical evaluation. But now, the combination of said triazine derivatives with insulin underlying the invention has been found to synergistically act in improving the control of glucose metabolism. The present invention reveals a strong glucose homeostasis improvement. These phenomena are stimulated by the impact of the composition of insulin with compounds of formula (I), which forms the basis of the inventive combined remedy for such specified clinical pictures as insulin-dependent diabetes mellitus (IDDM), non-insulin dependent diabetes mellitus (NIDDM) and the metabolic syndrome.

The composition of the invention exhibits very valuable pharmacological properties along with good tolerability. In comparison with a standard insulin therapy, the doses of insulin, which has to be administered, can be significantly reduced if combined with a triazine derivative of formula (I), thereby preventing weight gain at any dose of the composition as tested in pre-clinical trials. Consequently, the aforementioned compositions represents a novel combined medicament that is well suited for the prophylaxis, treatment and/or monitoring of IR and/or IR-mediated diseases. More particular, the inventive composition gives a potent anti-diabetic drug for a broad range of patients.

Said biological activities of the composition of the invention may be determined by techniques known to the skilled artisan. Suitable experimental animals are, for example, mice, rats, guinea-pigs, dogs, cats, apes or pigs. The gold standard for the in-vivo assessment of IR is the euglycemic-hyperinsulinemic glucose clamp. Other tools are the homeostasis model assessment of insulin resistance (HOMA-IR) or the frequently sampled oral glucose tolerance test (FSOGTT300-22), wherein 300-22 stands for 300 minutes with 22 samples. Techniques that are suitable to determine changes in insulin sensitivity have to be sensitive, reproducible, operationally simple and relatively high-throughput.

The recently developed, deuterated glucose disposal test ($^2$H-GDT) involving stable isotope-mass spectrometric assessment of whole-body glycolysis allows the assessment of IR by measuring the $^2$H$_2$O-production per unit of plasma insulin*glucose, which is based on the rate of release of deuterium ($^2$H) from an (oral) load of the animal or individual with deuterated [6,6'-$^2$H$_2$]glucose and the determined plasma insulin concentrations (Turner & Hellerstein (2005) Curr Opin Drug Discovery & Develop 8(1): 115-126). In addition, the degree of pancreatic β-cell compensation to IR can be assessed by measuring the absolute $^2$H$_2$O production achieved after the [6,6'-$^2$H$_2$]glucose load. Adequacy of pancreatic compensation can be assessed by distinguishing between the glycolytic disposal per unit of ambient insulin (reflecting insulin sensitivity) and the absolute rate of glucose utilization achieved (reflecting pancreatic compensation to IR). The $^2$H-GDT is designed to adhere to the following principles: i) ambient glucose and insulin concentrations should reflect metabolic conditions physiologically relevant, ii) the test should measure insulin-mediated glucose utilization by tissues and reveal IR in established models, and iii) the method should reflect comparable metabolic conditions as other tests of IR that are proven to be predictive for cardiovascular outcomes and T2DM risk. Serum insulin concentrations in the "dynamic range" between basal and maximal glucose utilization conditions fulfill these criteria (Beysen et al. (2007) Diab Care 30:1143-1149). Furthermore, the $^2$H-GDT, which measures the whole-body glycolysis in animals or humans in a quantitative manner, strongly correlates with the euglycemic-hyperinsulinemic glucose clamp. The utilization of said kinetic assay is consequently preferred in the scope of the invention in order to determine the in-vivo effect of an agent on insulin sensitivity as well as insulin compensatory responses, in particular at relatively high-throughput, and in many commonly used preclinical animal models. In addition, the $^2$H-GDT is completely translational into the clinical setting with a similar degree of simplicity and throughput.

In the meaning of the present invention, the compound of formula (I) is defined to include pharmaceutically usable derivatives comprising solvates, prodrugs, tautomers, enantiomers, racemates and stereoisomers thereof, including mixtures thereof in all ratios. Preference is given to solvates and/or physiologically acceptable salts, more preferably physiologically acceptable salts, most preferably physiologically acceptable acid-addition salts.

The term "solvates" of the triazine derivatives is taken to mean adductions of inert solvent molecules onto the compounds, which are formed owing to their mutual attractive force. Solvates are, for example, mono- or dihydrates or alkoxides.

The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115: 61-67 (1995). The compound of the invention can be obtained by liberating it from their functional derivatives by solvolysis, in particular hydrolysis, or by hydrogenolysis. It is likewise possible for the compounds of the invention to be in the form of any desired prodrugs, such as esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth et al. (1996) The Practice of Medicinal Chemistry, Chapter 31: 671-696, Academic Press; Bundgaard, H. (1985) Design of Prodrugs, Elsevier; Bundgaard, H. (1991) A Textbook of Drug Design and Development, Chapter 5: 131-191, Harwood Academic Publishers). It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers.

Formula (I) also encompasses the optically active forms (stereoisomers), such as the enantiomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. For example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds. The composition may also comprise mixtures of the compound and at least a singe derivative, or mixtures of derivatives, respectively, which may comprise solvates and/or salts, for instance.

The nomenclature as used herein for defining compounds, especially the compounds according to the invention, is in general based on the rules of the IUPAC-organization for chemical compounds and especially organic compounds. The terms indicated for explanation of the above compounds of the invention always, unless expressly indicated otherwise in the description or in the claims, have the following meanings:

Above and below, the radicals $R^1$, $R^2$, $R^3$, $R^4$, $R^5$, $R^6$ have the meanings indicated for the formula (I), unless expressly indicated otherwise.

A denotes alkyl, which is unbranched (linear) or branched and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl. Furthermore, A preferably denotes alkyl having 1, 2, 3, 4, 5 or 6 C atoms, more preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Very particularly preferably, A denotes methyl.

Cyclic alkyl (cycloalkyl) preferably denotes cyclopropyl, cyclobutyl, cyclopentyl, cyclohexyl or cycloheptyl.

Alkenyl has 2, 3, 4, 5 or 6 C atoms and preferably denotes vinyl or propenyl.

Alkynyl has 2, 3, 4, 5 or 6 C atoms and preferably denotes $C\equiv CH$ or $C\equiv C-CH_3$.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonyl)phenyl, o-, m- or p-cyanophenyl, o-, m- or p-carboxyphenyl, o-, m- or p-methoxycarbonylphenyl, o-, m- or p-acetylphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-amino-4-chloro-, 2-amino-3-chloro-, 2-amino-4-chloro-, 2-amino-5-chloro- or 2-amino-6-chlorophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-fluoro-4-methoxyphenyl, 3-amino-6-methylphenyl or 2,5-dimethyl-4-chlorophenyl. Ar particularly preferably denotes phenyl, hydroxyphenyl or methoxyphenyl.

Irrespective of further substitutions, Het denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated. Irrespective of further substitutions, Het can thus, for example, also denote 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindolyl, 2-oxo-1,3-dihydroindolyl or 2-oxo-2,3-dihydrobenzimidazolyl.

Het preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl or benzo-2,1,3-thiadiazolyl, each of which is unsubstituted or mono-, di- or trisubstituted by A, COOA, Hal and/or =O (carbonyl oxygen).

$R^1$ and $R^2$ preferably denote A. $R^3$ and $R^4$ preferably denote H. $R^5$ preferably denotes H. $R^6$ preferably denotes A. More preferably, $R^1$ and $R^2$ denote methyl, $R^3$ and $R^4$ denote H, $R^5$ denotes H, and $R^6$ denotes methyl.

In a most preferably embodiment of the present invention, the composition comprises the compound 5,6-dihydro-4-dimethylamino-2-imino-6-methyl-1,3,5-triazine. In a highly preferred embodiment of the present invention, the composition comprises the enantiomer (+) 5,6-dihydro-4-dimethylamino-2-imino-6-methyl-1,3,5-triazine.

The triazine derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

According to EP 1 250 328 B1, whose disclosure is incorporated in its entirety by reference herein, the compounds of formula (I) can be prepared by reacting a compound of formula (II)

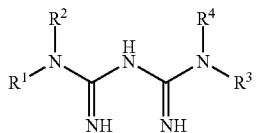

in which
$R^1$, $R^2$, $R^3$, $R^4$ have the meanings indicated above, with a compound of the formula (III), (IV) or (V)

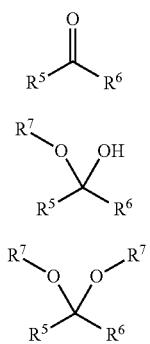

in which
$R^5$, $R^6$ have the meanings indicated above, and
$R^7$ is a methyl or ethyl group,
wherein the reaction is performed in a polar solvent (e.g. ethanol or dimethylformamide) and in the presence of an organic (e.g. camphorsulfonic acid) or inorganic acid (e.g. hydrochloric acid).

It is preferred, however, that the compounds of formula (I) are prepared by a process, which comprises the reaction of a compound of formula (II)

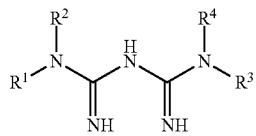

in which
$R^1$, $R^2$, $R^3$, $R^4$ have the meanings indicated above, with a compound of the formula (VI)

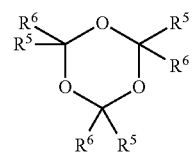

in which
$R^5$, $R^6$ have the meanings indicated above.

Surprisingly, investigations in the course of the synthesis of dihydro-1,3,5-triazinamine derivatives showed that the compounds of formula (I) can be obtained in at least comparable or higher yield compared to the prior art. Crucial advantages that may be mentioned here are a considerably shorter reaction time and fewer waste products. This consequently also means considerably lower energy consumption. One molecule of water is liberated in the process according to the invention per molecule of compound of the formula (I) formed. In the prior-art process, two molecules of alcohol are liberated per molecule of compound of the formula (I) formed.

Metformin as preferred starting material has the structure:

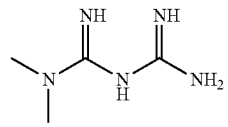

The compounds having the general formula (II) are biguanides, the synthesis of which is mastered by the average person skilled in the art. Some publications in which the synthesis of such compounds is described are cited by way of example (FR 1 537 604; FR 2 132 396; Slotta & Tschesche (1929) Ber. 62b: 1398; Shapiro et al. (1959) J. Org. Chem. 81: 3725, 3728, 4636).

The reaction of the compounds of the formulae (II) and (III) preferably proceeds in a suitable polar solvent, e.g. alcohols, such as methanol, ethanol, isopropanol, n-propanol, n-butanol, isobutanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); esters, such as ethyl acetate, or mixtures of the said solvents. Particular preference is given to isobutanol, furthermore ethanol and isopropanol.

Depending on the conditions used, the reaction time is between a few minutes and 14 days, particularly preferably between 3 and 12 hours. The reaction temperature is between about 50° C. and 150° C., normally between 90° C. and 120° C.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods.

The reaction is preferably carried out in the presence of an organic or inorganic acid. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Also suitable and preferred in the meaning of the present invention are acidic cationic ion exchanger resins, such as the commercially available Dowex® or Amberlyst® resins. More preference is given to p-toluenesulfonic acid, furthermore hydrochloric acid, methanesulfonic acid, sulfuric acid or camphorsulfonic acid, or acidic cationic ion exchanger resins, for example Dowex® 50, Amberlyst® 15 or Dowex® DR-2030. Most preferably, the reaction is carried out in the presence of p-toluenesulfonic acid or an acidic cationic ion exchanger resin.

A base of the formula (I) can also be converted into the associated acid-addition salt using an acid, for example by reaction of equivalent amounts of the base and acid in an inert solvent, such as ethanol, with subsequent evaporation. Particularly suitable acids for this reaction are those which give physiologically acceptable salts. Thus, it is possible to use inorganic acids, for example the aforementioned ones. Salts with physiologically unacceptable acids, for example picrates, can be used for the isolation and/or purification of the compounds of the formula (I).

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

In a very preferred aspect of the present invention, the composition comprises 5,6-dihydro-4-dimethylamino-2-imino-6-methyl-1,3,5-triazine hydrochloride. In another highly preferred embodiment of the present invention, the composition comprises the enantiomeric compound salt (+) 5,6-dihydro-4-dimethylamino-2-imino-6-methyl-1,3,5-triazine hydrochloride.

Insulin, which represents the other component of the composition according to the invention, is a hypoglycemiant hormone of polypeptide nature, which may be obtained according to many known methods. These methods may more particularly be chemical, semi-synthetic, biological (especially by simple extraction of human or animal insulin) or biogenetic (by expression of recombinant insulin). For the purposes of the invention, the term "insulin" includes insulin analogues that have structural differences with human insulin, but do not significantly modify the biological activity compared with human or animal insulin. Thus, insulin analogues that may especially be mentioned include Insuman® (Aventis), Organosuline® (Organon), Humalog® (Insulin lispro from Lilly), Lantus® (Insulin Glargin from Aventis) and Novolog® (Insulin Aspart from Novo Nordisk).

As set forth above, the invention relates to a medicament comprising insulin and at least one triazine compound and/or derivative thereof according to the invention, and optionally excipients and/or adjuvants. In the meaning of the invention, an "adjuvant" denotes every substance that enables, intensifies or modifies a specific response against the active ingredients of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols. In the meaning of the invention, the term "adjuvant" also includes the expressions "excipient" and "pharmaceutically acceptable vehicle", which denote any solvent, dispersing medium, absorption retardants, etc. that do not cause a side action, for example an allergic reaction, in humans or animals. Consequently, the invention also relates to a pharmaceutical composition comprising as active ingredients an effective amount of insulin and an effective amount of at least one compound of formula (I) as defined in the course of the present specification and/or physiologically acceptable salts thereof together with pharmaceutical tolerable adjuvants.

A "medicament", "pharmaceutical composition" or "pharmaceutical formulation" in the meaning of the invention is any agent in the field of medicine, which comprises insulin in combination with one or more triazine compounds of the invention or preparations thereof and can be used in prophylaxis, therapy, follow-up or aftercare of patients who suffer from diseases, which are associated with IR, in such a way that a pathogenic modification of their overall condition or of the condition of particular regions of the organism could establish at least temporarily.

Furthermore, the active ingredients may be administered alone or in combination with yet other treatments. Another synergistic effect may be achieved by using more than one compound of formula (I) in the pharmaceutical composition. It is also possible that insulin and the compound of formula (I) are combined with at least another agent of different structural scaffold as active ingredient. All active ingredients can be used either simultaneously or sequentially.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredients with the excipient(s) or adjuvant(s). The pharmaceutical compositions of the invention may be formulated such as to be administered to the patient via a single route (for example by injection) or via different routes (for example orally for the compound of the formula (I) and by injection for insulin).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient(s) to produce a single dosage form varies depending upon the host treated and the particular mode of administration. Suitable excipients include organic or inorganic substances that are suitable for the different routes of administration, such as enteral (e.g. oral), parenteral or topical application, and which do not react with the active ingredients of the invention or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions. Thus, for example, in the case of oral administration in the form of a tablet or capsule, the active ingredients can be combined with an oral, non-toxic and pharmaceutically acceptable inert excipient, such as, for example, ethanol, glycerol, water and the like. Powders are prepared by comminuting the active ingredients, especially the compounds, to a suitable fine size and mixing it with a pharmaceutical excipient comminuted in a similar manner, such as, for example, an edible carbohydrate, such as, for example, starch or mannitol. A flavor, preservative, dispersant and dye may likewise be present. Capsules are produced by preparing a powder mixture as described above and filling shaped gelatin shells therewith. Glidants and lubricants, e.g. highly disperse silicic acid, talc, magnesium stearate, calcium stearate or polyethylene glycol in solid form, can be added to the powder mixture before the filling operation. A disintegrant or solubiliser, such as agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the active ingredients, especially the compounds, comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The active ingredients according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the active ingredients. Syrups can be prepared by dissolving the active ingredients in an aqueous solution with a suitable flavor, while elixirs are prepared using a non-toxic alcoholic vehicle. Suspensions can be formulated by dispersion of the active ingredients, especially the compounds, in a non-toxic vehicle. Solubilisers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can be administered in the form of liposome delivery systems, such as small unilamellar vesicles, large unilamellar vesicles and multilamellar vesicles. Liposomes can be formed from various phospholipids, such as cholesterol, stearylamine or phosphatidylcholines.

The compounds according to the invention can also be fused or complexed with another molecule that promotes the directed transport to the destination, the incorporation and/or distribution within the target cells. The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and cross-linked or amphipathic block copolymers of hydro-gels.

Pharmaceutical formulations adapted for transdermal administration can be administered as independent plasters for extended, close contact with the epidermis of the recipient. Thus, for example, the active ingredients can be delivered from the plaster by iontophoresis, as described in general terms in Pharmaceutical Research, 3(6), 318 (1986).

Pharmaceutical compositions adapted for topical administration can be formulated as ointments, creams, suspensions, lotions, powders, solutions, pastes, gels, sprays, aerosols or oils. For the treatment of the eye or other external tissue, for example mouth and skin, the formulations are preferably applied as topical ointment or cream. In the case of formulation to give an ointment, the active ingredients can be employed either with a paraffinic or a water-miscible cream base. Alternatively, the active ingredients can be formulated to give a cream with an oil-in-water cream base or a water-in-oil base. Pharmaceutical formulations adapted for topical application to the eye include eye drops, in which the active ingredients are dissolved or suspended in a suitable carrier, in particular an aqueous solvent. Pharmaceutical formulations adapted for topical application in the mouth encompass lozenges, pastilles and mouthwashes.

Pharmaceutical formulations adapted for rectal administration can be administered in the form of suppositories or enemas. For the preparation of suppositories, the active principles are mixed in a manner that is known per se with a suitable base constituent, such as polyethylene glycol or semi-synthetic glycerides.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil. Pharmaceutical formulations adapted for administration by inhalation encompass finely particulate dusts or mists, which can be generated by various types of pressurized dispensers with aerosols, nebulisers or insufflators. Insulin and the compound of formula (I) may be administered by inhalation. The efficacy of inhalation of insulin is especially discussed by Skyler et al. (2001) Lancet 357(9253): 331-335. For example, aerosols and inhalation methods developed by Inhale Therapeutic Systems, Calif., and described in U.S. Pat. No. 5,997,848 make it possible to optimize the absorption and the reproducibility of the dose delivered.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets. The composition comprising insulin is preferably intended for parenteral administration, more particularly by injection.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably parenterally, most preferably as injection solution for parenteral administration. In particular, the active ingredients are provided in a water-soluble form, such as pharmaceutically acceptable salts, which is meant to include both acid and base addition salts. Furthermore, the active ingredients of the invention and salts thereof may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The respective dose or dosage range for administering the pharmaceutical composition according to the invention is sufficiently high in order to achieve the desired prophylactic or therapeutic effect of reducing symptoms of diseases, which are associated with IR, as set forth below. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1.000 mg, more preferably between 1 and 700 mg. It is even most preferred that the unit dose of the compound of formula (I) comprises 12.5 to 200 mg of said compound. It is also preferred that the unit dose of insulin comprises 10 to 400 IU (international units) of insulin, more preferably 0.1 to 1 IU.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of IR and/or pathologies associated with IR syndrome, for example diabetes, is generally in the range from 0.02 to 200 mg/kg of body weight of the recipient (mammal) per day and particularly typically in the range from 10 to 180 mg/kg of body weight per day, more preferably from 70 to 160 mg/kg, most preferably from 75 to 150 mg/kg. Thus, the actual amount per day for an adult mammal weighing 70 kg is usually between 14 and 14.000 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions as mentioned in the specification.

This composition contains therapeutically effective amounts of the various active principles. The ratios of the respective amounts of insulin and the compound of the formula (I) vary in consequence. In particular, the daily insulin dosage ranges between 0.5 and 1.0 IU per kg of body weight and the daily dosage of the compound of formula (I) ranges between 25 and 200 mg, in each case for an adult.

Accordingly, the inventive method of treatment can be employed in human and veterinary medicine. According to the invention, the compounds of formula (I) and/or physiologically salts thereof are suited for the prophylactic or therapeutic treatment and/or monitoring of diseases that are associated with IR, or IR itself, respectively. Herein, the compounds can be administered before or following an onset of disease once or several times acting as therapy. The aforementioned medical products of the inventive use are particularly used for the therapeutic treatment. Monitoring is considered as a kind of treatment, wherein the compounds are preferably administered in distinct intervals, e.g. in order to booster the response and eradicate the pathogens and/or symptoms of IR-related diseases completely. Either the identical composition or different compositions can be applied. The medicament can also be used to reduce the likelihood of developing a disease or even prevent the initiation of diseases associated with IR in advance or to treat the arising and continuing symptoms. In the meaning of the invention, prophylactic treatment is advisable if the subject possesses any preconditions for the aforementioned physiological or pathological conditions, such as a familial disposition, a genetic defect, or a previously passed disease.

The diseases as concerned by the invention are selected from the group of diabetes, pre-diabetes, low glucose tolerance, hyperglycemia, metabolic syndrome, diabetic nephropathy, neuropathy, retinopathy, arteriosclerosis and cardiovascular disease, furthermore vascular restenosis, pancreatitis and neurodegenerative disease.

In a preferred embodiment of the present invention, the disease is the metabolic syndrome. The medical indication "metabolic syndrome" is a combination of medical disorders that increase the risk of developing cardiovascular diseases. In addition to central obesity, two further symptoms and features have to be fulfilled for classification as the metabolic syndrome: fasting hyperglycemia (expressed by T2DM, impaired fasting glucose, impaired glucose tolerance or insulin resistance), high blood pressure and lipometabolic disorder (e.g. decreased HDL cholesterol and/or elevated triglycerides).

In another preferred embodiment of the invention, the composition of the invention is suitable for treating one or more pathologies associated with IR syndrome, which are chosen from dyslipidemia, obesity, arterial hypertension, macro-vascular complications, particularly atherosclerosis, and micro-vascular complications, particularly retinopathies, nephropathies and neuropathies. In a more preferred embodiment of the invention, the diseases are nephropathy and/or neuropathies. The medical indication "nephropathy" relates to diseases of the kidney and kidney function, which are mainly caused non-inflammatorily. The challenging subtype in the scope of the invention is reflected by diabetic nephropathy (nephropatia diabetica), which is also known as Kimmelstiel-Wilson syndrome and intercapillary glomerulonephritis. It is a progressive kidney disease caused by angiopathy of capillaries in the kidney glomeruli, and characterized by nephrotic syndrome and nodular glomerulosclerosis. It is due to long-standing diabetes mellitus, and is a prime cause for dialysis in many Western countries. Furthermore, the medical indication "neuropathy" is usually short for peripheral neuropathy. Peripheral neuropathy is defined as deranged function and structure of peripheral motor, sensory, and autonomic neurons, involving either the entire neuron or selected levels. Neuropathies often arise secondarily from other diseases, such as diabetes mellitus, or neurotoxic substances, such as alcohol abuse.

It is still another preferred embodiment of the invention that the pharmaceutical composition is especially suitable for treating diabetes by displaying considerable action on the metabolic syndrome of IR. Thus, particular preference of the inventive medical indication is given to diabetes, more preferably diabetes mellitus, most preferably IDDM and NIDDM. It is highly preferred to reduce hyperglycemia of NIDDM. The composition is also well-suited for treating diabetics of any type including Type I diabetes and Type II diabetes, preferably Type I diabetes and/or Type II diabetes, more preferably T2DM, and in the various stages of the disease.

According to another aspect of the invention, insulin and at east one compound of formula (I) are administered simultaneously or sequentially, preferably in the form of separate pharmaceutical compositions, one comprising insulin in a pharmaceutically acceptable vehicle, the other comprising the compound of formula (I) in a pharmaceutically acceptable vehicle. It shah not be excluded, however, that and at least one compound of formula (I) can be combined in the same pharmaceutical composition and administered, in the context of the present invention, the terms "pharmaceutical combination" and "combined administration" refers to one or other of these aspects.

In more detail, "combined administration" means, for the purpose of the present invention, fixed and, in particular, free combinations, i.e. either insulin and the compound of formula (I) are present together in one dosage unit, or insulin and said compound, which are present in separate dosage units, are administered in direct succession or at a relatively large time interval; a relatively large time interval means a time span up to a maximum of 24 hours. A "dosage unit" means, in particular, a medicinal dosage form in which the release of the active ingredient(s) is achieved with as few problems as possible. This includes, in particular, tablets, coated tablets or pellets, micro-tablets in capsules and solutions with the dosage form advantageously being designed such that the two active-ingredient components (insulin on the one hand and said compound of formula (I) on the other hand) are released, or made available effectively for the body, in such a way that an optimal active ingredient profile, and thus action profile, is achieved.

For simultaneous administration as fixed composition, i.e. being a single pharmaceutical formulation with both ingredients, it is prepared, for example, as injection or infusion solution, or lyophilized form thereof, which is filled in ampoules. The fixed composition of the lyophilized form guarantees a simple and secure handling. It is solved in the ampoule by adding an ordinary pharmaceutical injection agent and administered intravenously. The reconstitution solution can be part of the combination package. For use as separate dosage units, these are preferably made available together in one pack and either mixed prior administration or sequentially administered. For example, the two dosage units are packed together in blister packs that are designed with regard to the relative arrangement of the two dosage units with respect to one another, the inscription and/or coloring in a manner known per se so that the times for taking the individual components (dosage regimen) of the two dosage units are evident to a patient. This tree combination is of benefit by individually allotting an effective amount of insulin and an effective amount of the compound of formula (I) to the patient. Another possibility is the provision of single preparations of insulin and said compound, i.e. being independent medicaments. The single preparations are converted to contain the required amounts of ingredient for the inventive combination. Corresponding instructions are given at the package insert concerning the combined administration of the respective medicament.

Further, the invention may be practiced as a pharmaceutical package comprising as active ingredients an effective amount of insulin, together with one or more pharmaceutically acceptable adjuvants, in a first dosage unit, and an effective amount of at least one compound of formula (I) as defined above and/or physiologically acceptable salts thereof, together with one or more pharmaceutically acceptable adjuvants, in a second dosage unit, particularly in order to perform the prophylactic or therapeutic treatment and/or monitoring of diseases that are associated with IR. The package of the invention may include an article that comprises written instructions or directs the user to written instructions for how to practice the method of the invention. The prior teaching of the present specification concerning the composition and its administration is considered as valid and applicable without restrictions to the pharmaceutical package if expedient.

The invention also relates to the use of insulin in combination with at least one compound of formula (I) as defined according to the invention and/or physiologically acceptable salts thereof for the prophylactic or therapeutic treatment and/or monitoring of diseases that are associated with IR. Furthermore, the invention relates to the use of insulin in combination with at least one compound of formula (I) as defined according to the invention and/or physiologically acceptable salts thereof for the manufacture of a medicament for the prophylactic or therapeutic treatment and/or monitoring of diseases that are associated with IR. The medicament can be used to prevent the initiation of diseases associated with IR in advance or to treat the arising and continuing symptoms. The diseases as concerned by the invention are preferably diabetes and/or related diseases thereof, the latter are more preferably selected from the group of the metabolic syndrome, diabetic nephropathy and neuropathy. In addition, the prior teaching of the present specification concerning the inventive composition is valid and applicable without restrictions to the use of the composition and its salts for the manufacture of a medicament for prophylaxis and therapy of said diseases.

Object of the present invention is also the use of insulin in combination with at least one compound of formula (I) as defined herein and/or physiologically acceptable salts thereof for the enhancement of glucose homeostasis. Herein, "enhancement" refers to parameter values that exceed initial reading, within a normal statistical range as caused by the measurement method and the fact of a living organism involved. Glucose tolerance and/or insulin secretion in response to glucose represent preferred parameters for assessing glucose homeostasis, wherein the increase of one or both parameters indicates enhanced glucose homeostasis. The glucose tolerance and/or insulin secretion, particularly the insulin secretion, are preferably increased by at least 10%, more preferably at least 20%, and most preferably at least 30%. Such increase is preferably obtained if the compound of formula (I) is provided for administration in a dose range from 25 to 200 mg per kg of body weight, more preferably in a dose range from 75 to 150 mg per kg of body weight. The use may be either performed in-vitro or in-vivo models. The in-vitro use is preferably applied to samples of humans suffering from IR, more preferably IDDM or NIDDM. For example, testing of several compounds of formula (I) and/or mixtures with insulin makes the selection of that composition possible that is best suited for the treatment of the mammalian subject.

The in-vivo dose rate of the chosen derivative is advantageously pre-adjusted to the severity of IR of the respective specific cells with regard to the in-vitro data. Therefore, the therapeutic efficacy is remarkably enhanced. Moreover, the prior teaching of the present specification concerning the composition of the invention is considered as valid and applicable without restrictions to the use of the compound for the decrease of IR if expedient.

The invention is directed more particularly towards the use as defined above, in which insulin and the compound of formula (I) are in forms suitable for simultaneous administration. Alternatively, the invention is also directed towards the use as defined above, in which insulin and the compound of formula (I) are in forms suitable for sequential administration.

It is another object of the invention to provide a method for treating diseases that are associated with insulin resistance, wherein an effective amount of insulin in combination with an effective amount of at least one compound of formula (I) as defined according to the invention and/or physiologically acceptable salts thereof are administered to a mammal in need of such treatment. The mammals to be treated are humans in particular. The preferred treatment is an oral or parenteral administration. The treatment of the patients suffering from IDDM or NIDDM, or people bearing a risk of developing such diseases on the basis of existing IR by means of the combined application of insulin and a triazine compound improves the whole-body insulin sensitivity and ameliorates IR in these individuals. Such improvement is preferably obtained if the compound of formula (I) is administered in a dose range from 25 to 200 mg per kg of body weight, more preferably in a dose range from 75 to 150 mg per kg of body weight. In another preferred aspect, the triazine compound 5,6-dihydro-4-dimethylamino-2-imino-6-methyl-1,3,5-triazine is used at different doses, more preferably 5,6-dihydro-4-dimethylamino-2-imino-6-methyl-1,3,5-triazine hydrochloride. Insulin can be administered via a well-known device. The prior teaching of the invention and its embodiments is valid and applicable without restrictions to the method of treatment if expedient.

In the scope of the present invention, a pharmaceutical composition comprising insulin and a triazine derivative of formula (I) is provided for the first time. The invention addresses the successful improvement of glucose homeostasis in patients with present IR and/or associated diseases, particularly type 1 diabetes, comparatively to the insulin treatment alone. As result of administering the pharmaceutical composition according to the invention, the insulin secretion is at least partially or even completely restored in response to glucose. In addition, the combination of insulin with triazine derivatives induces a strong potentiation of the effects of insulin. Hence, triazine derivatives of formula (I) can be advantageously associated with insulin to reduce the therapeutic doses of insulin, particularly in type 1 diabetic patients, but also in type 2 diabetic patients. A chronic treatment of both types of diabetic patients with such triazine derivatives in the presence of pellets of insulin is of special benefit for the decrease of fasting plasma glucose and increase of glucose tolerance, respectively, although any dosage regime improves the aforementioned parameters. Another important point is the shift of the glucose distribution towards lower levels. The use of the composition is a promising, novel approach for a broad spectrum of therapies causing a direct and immediate reduction of symptoms. The impact is of special benefit to efficiently combat IR and/or illnesses arising from IR. The compound and derivatives thereof are characterized by a high specificity and stability; low manufacturing costs and convenient handling. These features form the basis for a reproducible action, wherein the lack of cross-reactivity and adverse effects is included, and for a reliable and safe interaction with their matching target structures.

All the references cited herein are incorporated by reference in the disclosure of the invention hereby.

It is to be understood that this invention is not limited to the particular methods, specific substances, uses and kits described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a salt" includes a single or several different salts and vice versa, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again if the technical problem of the invention is solved.

In the following Figures and Tables, the compound 5,6-dihydro-4-dimethylamino-2-imino-6-methyl-1,3,5-triazine is abbreviated as EMD.

EXAMPLE 1

Figure 1:
FIG. 1 shows the effect of the combination of insulin and 5,6-dihydro-4-dimethylamino-2-imino-6-methyl-1,3,5-triazine on plasma glucose in a type 1 rat model.

Preparation of 4-amino-3,6-dihydro-2-dimethylamino-6-methyl-1,3,5-triazine hydrochloride Above and below, all temperatures are given in ° C. In the following examples, "conventional work-up" means: if necessary, water is added, the pH is, if necessary, adjusted to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallization.

Comparative experiment) A mixture of 250.2 g of metformin hydrochloride, 213.6 g of acetaldehyde diethyl acetal and 12.5 g of toluene-4-sulfonic acid monohydrate in 500 ml of isobutanol was heated under reflux for 40 hours. Some of the solvent was removed by distillation. The mixture was cooled to 10° C., and the white precipitate was separated off, giving 224.7 g (77.4%) of 4-amino-3,6-dihydro-2-dimethylamino-6-methyl-1,3,5-triazine hydrochloride.

A) A mixture of 1002.6 g of metformin hydrochloride, 359.1 g of paraldehyde and 51.6 g of toluene-4-sulfonic acid monohydrate in 2405.9 g of isobutanol was heated under reflux for 6 hours. Some of the solvent was removed by distillation. The mixture was cooled to 12° C., and the white precipitate was separated off, giving 953.8 g (81.4%) of 4-amino-3,6-dihydro-2-dimethylamino-6-methyl-1,3,5-triazine hydrochloride.

B) A mixture of 100.1 g of metformin hydrochloride, 36.5 g of paraldehyde and 4 g of Dowex DR-2030 in 237.8 ml of isobutanol was heated under reflux for 6 hours. The catalyst was subsequently filtered off, and some of the solvent was removed by distillation. The remainder of the solution was cooled to 10-15° C., and the white precipitate was separated off, giving 93.5 g (80.7%) of 4-amino-3,6-dihydro-2-dimethylamino-6-methyl-1,3,5-triazine hydrochloride.

EXAMPLE 2

Effect of short chronic treatment (4 weeks) with insulin pellets in association with 5,6-dihydro-4-dimethylamino-2-imino-6-methyl-1,3,5-triazine on glucose homeostasis The study was performed in hyperglycemic and hypoinsulinemic Type 1 rat models obtained by injection of high dose of Streptozotocin (STZ). Male Wistar rats (Charles River) were treated with STZ at 62.5 mg/kg IP. Rats were screened for baseline glucose levels three days after STZ injection. The animals with glucose levels below 35-40 mmol/l were excluded from this study. After selection, pellets of insulin were subcutaneously implanted (1+½ implants) at day 3. The release rate for each implant was 2 U per 24 h. In these experimental conditions each rat was infused with 3 U per 24 h of insulin for 40 days approximately (Limplant LINSHIN CANADA). 5,6-dihydro-4-dimethylamino-2-imino-6-methyl-1,3,5-triazine was orally administered at two doses, 75 and 150 mg/kg b.i.d., 10 days after induction of diabetes. Further experimental details are known to the skilled artisan, e.g. by the disclosure of WO 2003/092726, and can be easily modified as a matter of routine.

After implantation of insulin pellets the plasma insulin level was stable in each group (Table 2). In addition, insulin pellets significantly reduced plasma glucose to 21.46±3.1 mmol/l (Table 1, FIG. 1) in comparison with 44.65±1.54 mmol/l in the control group without insulin (data not shown) after 36 days.

After administration of 5,6-dihydro-4-dimethylamino-2-imino-6-methyl-1,3,5-triazine, the plasma glucose decreased more. This effect of 5,6-dihydro-4-dimethylamino-2-imino-6-methyl-1,3,5-triazine was dose dependent. At 75 mg/kg b.i.d., the hyperglycemia dropped at the end of treatment from 21.46±3.1 to 18.86±2.77 mmol/l, whereas the hyperglycemia dropped at the end of treatment with the higher dose of 150 mg/kg b.i.d. from 21.46±3.1 to 14.85±2.03 mmol/l (Table 1, FIG. 1).

The determination how quickly administered glucose is cleared form the blood was conducted by means of a glucose tolerance test. The glucose was orally given; so the common test was technically an oral glucose tolerance test (OGTT), which is well-known to the skilled artisan. The laboratory animal was fasting for 18 hours before it was administered a glucose solution. Blood was drawn at intervals (cf. Table 3) for measurement of glucose (blood sugar), and additionally insulin levels were measured to detect the degree of IR or deficiency, respectively. For diabetes screening, the most important sample is the 2 hour sample, whose blood sugar value is enhanced at mammals with diminished insulin secretion or IR.

Figure 2:
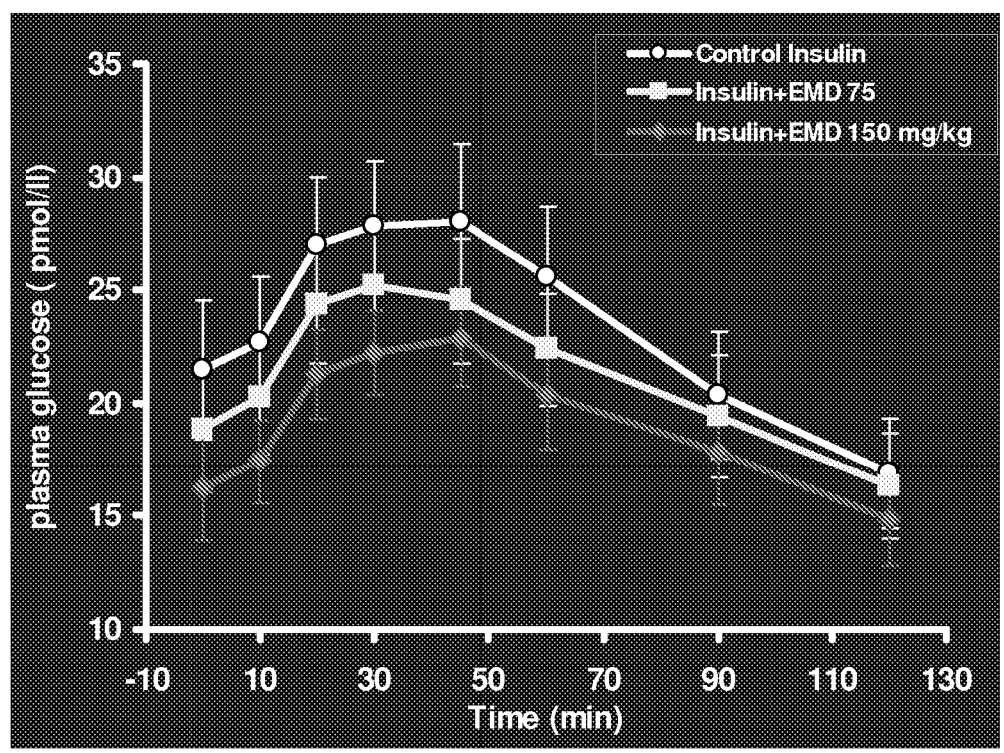
FIG. 2 shows the OGTT plasma glucose variations (mmol/l) after 36 days of treatment with the combination of insulin and 5,6-dihydro-4-dimethylamino-2-imino-6-methyl-1,3,5-triazine.

Comparatively to insulin alone, the combination of insulin with 5,6-dihydro-4-dimethylamino-2-imino-6-methyl-1,3,5-triazine improved the glucose tolerance, and this effect was also dose dependent (Table 3, FIG. 2). The higher the dose was, the better the rats tolerated glucose at an average. The detailed distribution of OGTT plasma glucose concentrations within each group is given below (cf. FIG. 4).

TABLE 1

Fasting plasma glucose (mmol/l) determination before and after treatment with the combination of insulin and 5,6-dihydro-4-dimethylamino-2-imino-6-methyl-1,3,5-triazine.

| | Days | | | | |
|---|---|---|---|---|---|
| | 0 | 8 | 15 | 22 | 36 |
| control + insulin | 33.20 | 17.22 | 11.25 | 16.66 | 21.46 |
| sem | 0.65 | 2.68 | 1.75 | 1.95 | 3.10 |
| EMD75 mg/kg + insulin | 33.37 | 18.60 | 11.42 | 17.59 | 18.86 |
| sem | 0.60 | 2.99 | 2.08 | 2.60 | 2.77 |
| EMD150 mg/kg + insulin | 33.39 | 19.22 | 10.17 | 13.13 | 14.85 |
| sem | 0.60 | 2.14 | 1.54 | 2.07 | 2.03 |

TABLE 2

Fasting plasma insulin (pmol/l) determination before and after treatment with the combination of insulin and 5,6-dihydro-4-dimethylamino-2-imino-6-methyl-1,3,5-triazine.

| | Days | | | | |
|---|---|---|---|---|---|
| | 0 | 8 | 15 | 22 | 36 |
| Control | 57 | 653 | 597 | 496 | 459 |
| sem | 12 | 76 | 59 | 29 | 56 |
| EMD 75 mg/kg | 63 | 666 | 602 | 592 | 475 |
| sem | 11 | 93 | 62 | 80 | 81 |
| EMD 150 mg/kg | 48 | 586 | 635 | 558 | 496 |
| sem | 8 | 82 | 77 | 39 | 50 |

Sem denotes the standard error of the mean.

TABLE 3

Plasma glucose variations (mmol/l) after 36 days of treatment with the combination of insulin and 5,6-dihydro-4-dimethylamino-2-imino-6-methyl-1,3,5-triazine as determined by OGTT.

| | min | | | | | | | |
|---|---|---|---|---|---|---|---|---|
| | 0 | 10 | 20 | 30 | 45 | 60 | 90 | 120 |
| Control Insulin | 21.46 | 22.73 | 26.98 | 27.83 | 28.04 | 25.59 | 20.35 | 16.91 |
| sem | 3.10 | 2.85 | 2.97 | 2.86 | 3.43 | 3.05 | 2.77 | 2.43 |
| Insulin + EMD 75 | 18.86 | 20.27 | 24.33 | 25.16 | 24.53 | 22.38 | 19.41 | 16.36 |
| sem | 2.77 | 2.49 | 2.60 | 2.71 | 2.74 | 2.48 | 2.68 | 2.35 |
| Insulin + EMD 150 mg/kg | 16.29 | 17.43 | 21.30 | 22.21 | 22.90 | 20.37 | 17.82 | 14.85 |
| sem | 2.35 | 1.80 | 1.98 | 1.88 | 2.21 | 2.43 | 2.30 | 2.05 |

Figure 3:
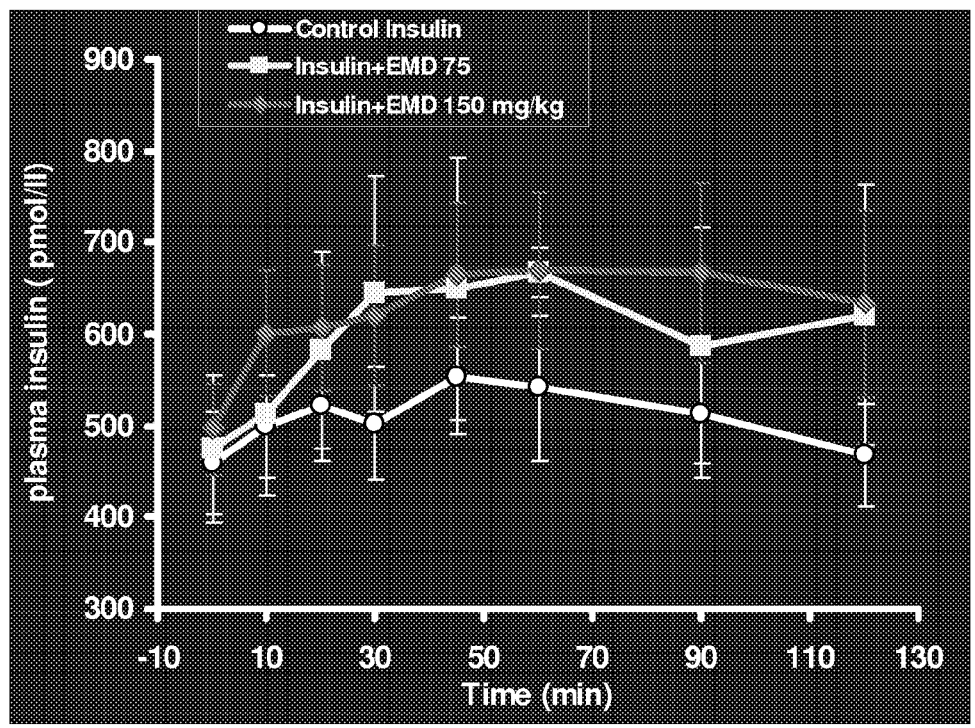
FIG. 3 shows the OGTT plasma insulin variations (pmol/l) after glucose load and 36 days of treatment with the combination of insulin (3 UI/day) and 5,6-dihydro-4-dimethylamino-2-imino-6-methyl-1,3,5-triazine.

Comparatively to insulin alone, the combination of insulin with 5,6-dihydro-4-dimethylamino-2-imino-6-methyl-1,3,5-triazine moderately increased the insulin secretion in response to glucose (FIG. 3).

Figure 4:
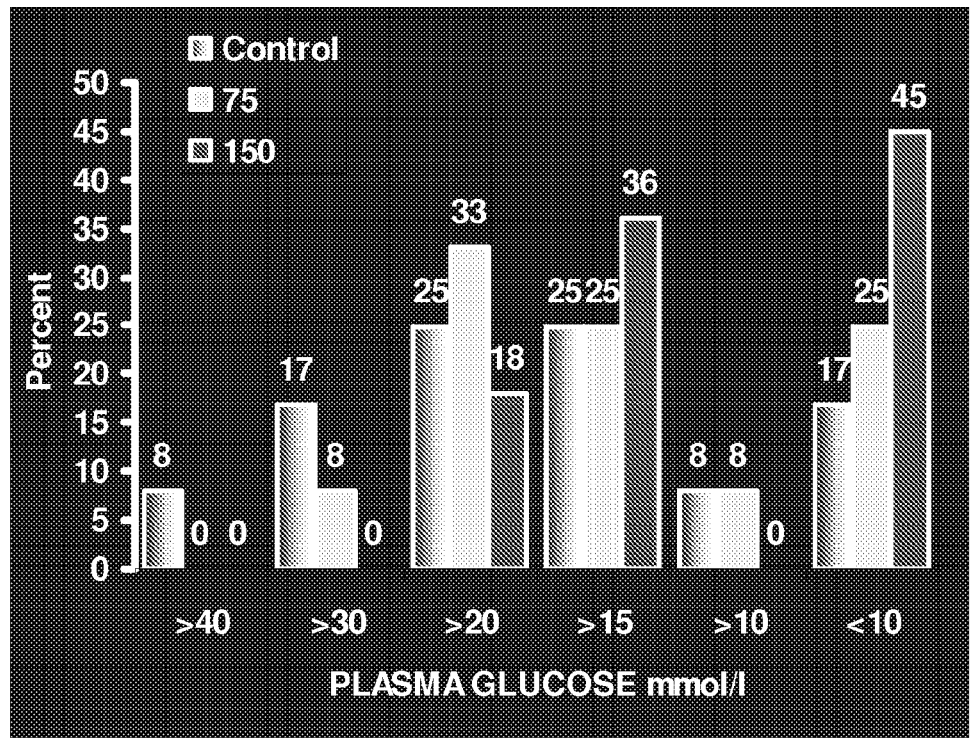
FIG. 4 shows the distribution (percent) of fasting hyperglycemia level for each group: control, insulin (3 UI/day)+5,6-dihydro-4-dimethylamino-2-imino-6-methyl-1,3,5-triazine (75 mg/kg b.i.d.) as well as insulin (3 UI/day)+5,6-dihydro-4-dimethylamino-2-imino-6-methyl-1,3,5-triazine (150 mg/kg b.i.d.).

The analysis of the distribution of fasting hyperglycemia levels showed that the combination of insulin with 5,6-dihydro-4-dimethylamino-2-imino-6-methyl-1,3,5-triazine shifted the repartition of plasma glucose concentrations toward lower levels. Almost 50% of rats treated with the combination of insulin and 150 mg/kg b.i.d. 5,6-dihydro-4-dimethylamino-2-imino-6-methyl-1,3,5-triazine showed a hyperglycemia level that was lower than 10 mmol/l (FIG. 4).

EXAMPLE 3

Pharmaceutical Preparations

A) Injection vials: A solution of 100 g of one or more active ingredients according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient(s).

B) Suppositories: A mixture of 20 g of one or more active ingredients according to the invention was melted with 100 g of soya lecithin and 1400 g of cocoa butter, poured into moulds and allowed to cool. Each suppository contained 20 mg of active ingredient(s).

C) Solution: A solution was prepared from 1 g of one or more active ingredients according to the invention, 9.38 g of $NaH_2PO_4.2H2O$, 28.48 g of $Na_2HPO_4.12H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

D) Ointment: 500 mg of one or more active ingredients according to the invention were mixed with 99.5 g of Vaseline under aseptic conditions.

E) Tablets: A mixture of 1 kg of one or more active ingredients according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient(s). Other tablets with the active ingredient 5,6-dihydro-4-dimethylamino-2-imino-6-methyl-1,3,5-triazine were prepared according to the Tables 4-9.

TABLE 4

Tablet containing 87% triazine derivative and adjuvants.

|  | mg | % |
|---|---|---|
| 5,6-dihydro-4-dimethylamino-2-imino-6-methyl-1,3,5-triazine | 200 | 87.0 |
| Lactose | 10.5 | 4.6 |
| Starch | 5.7 | 2.5 |
| Crospovidone | 5.7 | 2.5 |
| Talc | 7 | 3.0 |
| Magnesium stearate | 1.1 | 0.5 |
| Total | 230 | 100.0 |

TABLE 5

Tablet containing 43.5% triazine derivative and adjuvants.

|  | Mg | % |
|---|---|---|
| 5,6-dihydro-4-dimethylamino-2-imino-6-methyl-1,3,5-triazine | 100 | 43.5 |
| Mannitol | 50.5 | 22.0 |
| Avicel ph 102 | 60 | 26.1 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 6

Tablet containing 21.7% triazine derivative and adjuvants.

|  | Mg | % |
|---|---|---|
| 5,6-dihydro-4-dimethylamino-2-imino-6-methyl-1,3,5-triazine | 50 | 21.7 |

TABLE 6-continued

Tablet containing 21.7% triazine derivative and adjuvants.

|  | Mg | % |
|---|---|---|
| Mannitol | 80.5 | 35.0 |
| Avicel ph102 | 80 | 34.8 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 7

Tablet containing 87% triazine derivative and adjuvants.

|  | mg | % |
|---|---|---|
| 5,6-dihydro-4-dimethylamino-2-imino-6-methyl-1,3,5-triazine | 200 | 87.0 |
| Mannitol | 10.5 | 4.6 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 8

Tablet containing 79.4% triazine derivative and adjuvants.

|  | mg | % |
|---|---|---|
| 5,6-dihydro-4-dimethylamino-2-imino-6-methyl-1,3,5-triazine | 100 | 79.4 |
| Lactose | 12.2 | 9.7 |
| Hydroxypropylcellulose | 5.7 | 4.5 |
| Talc | 7 | 5.6 |
| Magnesium stearate | 1.1 | 0.9 |
| Total | 126 | 100.0 |

TABLE 9

Tablet containing 12.7% triazine derivative and adjuvants.

|  | Mg | % |
|---|---|---|
| 5,6-dihydro-4-dimethylamino-2-imino-6-methyl-1,3,5-triazine | 50 | 12.7 |
| Lactose | 172.2 | 43.7 |
| Avicel ph102 | 152 | 38.6 |
| Hydroxypropylcellulose | 7.1 | 1.8 |
| Sodium starch glycolate | 11.5 | 2.9 |
| Magnesium stearate | 1.2 | 0.3 |
| Total | 394 | 100 |

F) Coated tablets: Tablets were pressed analogously to the previous paragraph E) and subsequently coated in a conventional manner with a coating of sucrose, potato starch, talc, tragacanth and dye.

G) Capsules: 2 kg of one or more active ingredients according to the invention were introduced into hard gelatin capsules in a conventional manner in such a way that each capsule contained 20 mg of the active ingredient(s).

H) Ampoules: A solution of 1 kg of one or more active ingredients according to the invention in 60 l of bidistilled water was sterile filtered, transferred into ampoules, lyophilized under sterile conditions and sealed under sterile conditions. Each ampoule contained 10 mg of active ingredient(s).

I) Inhalation spray: 14 g of one or more active ingredients according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. A pharmaceutical composition comprising insulin in combination with at least one compound of formula (I) and/or physiologically acceptable salts thereof, wherein the compound of formula (I) is defined as follows:

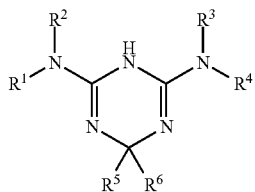

I in which
$R^1$, $R^2$ each, independently of one another, denote H or A,
$R^3$, $R^4$ each, independently of one another, denote H, A, alkenyl having 2-6 C atoms, alkynyl having 2-6 C atoms, Ar or Het,
$R^5$, $R^6$ each, independently of one another, denote H, A, $(CH_2)_n$Ar, $(CH_2)_m$OAr, $(CH_2)_m$OA or $(CH_2)_m$OH,
$R^5$ and $R^6$ together also denote alkylene having 2, 3, 4 or 5 C atoms, in which one $CH_2$ group may be replaced by O, NH or NA and/or in which 1 H atom may be replaced by OH,
Ar denotes phenyl, naphthyl or biphenyl, each of which is unsubstituted or mono-, di- or trisubstituted by Hal, A, OA, OH, COOH, COOA, CN, $NH_2$, NHA, $NA_2$, $SO_2A$ and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, OH, OA, $NH_2$, $(CH_2)_n$Ar, NHA, $NA_2$, COOH, COOA and/or =O (carbonyl oxygen),
A denotes unbranched or branched alkyl having 1-10 C atoms, in which 1-7 H atoms may be replaced by F, or cyclic alkyl having 3-7 C atoms,
Hal denotes F, Cl, Br or I,
m denotes 1, 2, 3, 4, 5 or 6, and
n denotes 0, 1 or 2.

2. Pharmaceutical composition comprising as active ingredients an effective amount of insulin in combination with an effective amount of at least one compound of formula (I) as defined in claim 1 and/or physiologically acceptable salts thereof, together with one or more pharmaceutically acceptable adjuvants.

3. Composition according to claim 1, wherein the compound of formula (I) is 5,6-dihydro-4-dimethylamino-2-imino-6-methyl-1,3,5-triazine.

4. Composition according to claim 1, wherein the insulin is in fixed combination with the compound of formula (I) in a single dosage unit.

5. Composition according to claim 1, wherein the insulin and the compound of formula (I) are in separate dosage units in a single package.

6. Pharmaceutical package comprising as active ingredients an effective amount of insulin, together with one or more pharmaceutically acceptable adjuvants, in a first dosage unit, and an effective amount of at least one compound of formula (I) as defined in claim 1 and/or physiologically acceptable salts thereof, together with one or more pharmaceutically acceptable adjuvants, in a second dosage unit.

* * * * *

UNITED STATES PATENT AND TRADEMARK OFFICE
CERTIFICATE OF CORRECTION

PATENT NO. : 8,592,370 B2  Page 1 of 1
APPLICATION NO. : 13/139027
DATED : November 26, 2013
INVENTOR(S) : Mesangeau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 107 days.

Signed and Sealed this
Twenty-second Day of September, 2015

Michelle K. Lee
*Director of the United States Patent and Trademark Office*